US008543422B2

(12) United States Patent (10) Patent No.: US 8,543,422 B2
Maman et al. (45) Date of Patent: Sep. 24, 2013

(54) PERSONALIZED MEDICAL CONTENT RECOMMENDATION

(75) Inventors: Yonatan Maman, Hof Hacarmel (IL); Yossi Mesika, Afula (IL); Haggai Roitman, Yoknea'm Elit (IL)

(73) Assignee: International Business Machines Corporation, Armonk, NY (US)

( * ) Notice: Subject to any disclaimer, the term of this patent is extended or adjusted under 35 U.S.C. 154(b) by 198 days.

(21) Appl. No.: 13/079,033

(22) Filed: Apr. 4, 2011

(65) Prior Publication Data

US 2012/0253139 A1 Oct. 4, 2012

(51) Int. Cl.
*G06Q 50/24* (2012.01)

(52) U.S. Cl.
USPC .................................... 705/3; 705/2

(58) Field of Classification Search
USPC .......................... 600/300; 705/2, 3
See application file for complete search history.

(56) References Cited

U.S. PATENT DOCUMENTS

| | | | | |
|---|---|---|---|---|
| 5,974,412 A | * | 10/1999 | Hazlehurst et al. | 1/1 |
| 6,526,440 B1 | * | 2/2003 | Bharat | 709/219 |
| 6,725,259 B1 | * | 4/2004 | Bharat | 709/219 |
| 7,431,701 B2 | * | 10/2008 | Schmidt | 600/587 |
| 7,809,585 B1 | | 10/2010 | Ghouri | |
| 2006/0106647 A1 | | 5/2006 | Brummel et al. | |
| 2006/0143050 A1 | * | 6/2006 | Dean | 705/3 |
| 2007/0203903 A1 | * | 8/2007 | Attaran Rezaei et al. | 707/5 |
| 2008/0005095 A1 | * | 1/2008 | Horvitz et al. | 707/5 |
| 2009/0006374 A1 | * | 1/2009 | Kim et al. | 707/5 |
| 2009/0187418 A1 | * | 7/2009 | Sioui | 705/2 |
| 2009/0216558 A1 | * | 8/2009 | Reisman et al. | 705/3 |
| 2009/0216563 A1 | * | 8/2009 | Sandoval et al. | 705/3 |
| 2010/0235193 A1 | * | 9/2010 | McGuigan et al. | 705/2 |
| 2010/0280333 A1 | * | 11/2010 | Parshuram et al. | 600/301 |

FOREIGN PATENT DOCUMENTS

WO WO 2007/079181 * 7/2007

OTHER PUBLICATIONS

Rasolofo, Yves; "Term Proximity Scoring for Keyword-Based Retrieval Systems"; 2003; Computer Science 2633, 1611-3349.*
David Goldberg et al., "Using collaborative filtering to weave an information tapestry". Commun. ACM,35(12):61-70, 1992.
M. J. Pazzani and D. Billsus, "Content-based recommendation systems". 2007.
S. S. R. Abidi et al., "Patient empowerment via pushed delivery of personalized healthcare educational content over the internet". In Proceedings of 10th World Congress on Medical Informatics, 2001. World Bank, 2001.

(Continued)

*Primary Examiner* — Gerald J. O'Connnor
*Assistant Examiner* — John Go

(57) ABSTRACT

Method, system, and computer program product for personalized medical content recommendation are provided. The method may comprise having a patient medical profile; having a concept or relationship relating to the patient medical profile; obtaining medical content relevant to the concept or relationship; determining a score of the concept or relationship to the patient medical profile; enhancing the score with a context score based on the values of attributes of the concept or relationship in the patient medical profile; enhancing the score with an additional knowledge score based on knowledge of the concept or relationship additional to the medical content; recommending medical content with respect to a patient medical profile based on the enhanced scores. The method may also include providing an explanation of a medical content recommendation based on a matching concept or relationship.

15 Claims, 6 Drawing Sheets

(56) References Cited

OTHER PUBLICATIONS

Persephone Doupi et al., "Personalizing patient education using internet health resources and epr data: Pilot evaluation of the stepps prototype system". In CBMS '08.

Haggai Roitman et al., "Increasing Patient Safety using Explanation-Driven Personalized Content Recommendation", IHI 2010 Arlington, VA. Copyright 2010 ACM.

Shima Gerani, et al., "Proximity-Based Opinion Retrieval", Proceeding of the 33rd international ACM SIGIR conference on Research and Development in Information Retrieval, 2010.

* cited by examiner

PERSONALIZED MEDICAL CONTENT RECOMMENDATION

BACKGROUND

This invention relates to the field of medical content recommendation. In particular, the invention relates to personalized medical content recommendation.

In recent years, it has been recognized that errors in medical decision making processes can lead to disastrous outcomes. Both governmental and private healthcare organizations are concerned with patient safety, realizing that improvements in patient safety can help to minimize healthcare risks and increase recovery rates. Many organizations invest a lot of money every year in exploring new ways for improving patients' safety. New dedicated IT solutions for the patient safety domain are continuously being explored, aiming at helping to prevent mistakes by medical teams and patients due to erroneous decisions. Some of these solutions are targeted at personalization of medical content recommendations to patients gathered from public web sources.

Drug overdosing or underdosing, or the consumption of some drug together with other drugs or foods, may result in undesirable outcomes of adverse drug events (ADEs), which may be life threatening and even lead to death. According to the Agency for Healthcare Research and Quality (AHRQ), ADEs result in more than 770,000 injuries and deaths every year, costing up to 5.6 million dollars per hospital per year. Furthermore, patients who experience ADEs are hospitalized an average of 8 to 12 days longer than patients who do not suffer from ADEs; this in turn, results in additional 16,000 to 24,000 dollars on average in hospitalization costs.

It is estimated that anywhere from 28% to 95% of ADEs could be prevented by reducing medication errors. There are many useful drug and ADE related knowledge sources available on the web that can be utilized to discover existing or even new potential ADEs and provide timely alerts to relevant patients. To name few examples of such sources, are governmental health monitoring services such as the U.S. Food and Drug Administration (FDA) MedWatch alerting service that publish updates related to various patient safety and ADE related topics, online medical digital libraries such as PubMed (PubMed is a trade mark of National Library of Medicine, The Federal Agency United States) that provide updates about new published ADE-related research works, and online ADE knowledge sources such as DrugBank and SIDER (Side Effect Resource) that provide access to various knowledge about drug interactions and side-effects using semantic web technology. Other drug-related websites such as Drugs.com and MedlinePlus (MedlinePlus is a trade mark of National Library of Medicine, The Federal Agency United States) also provide valuable information about various drugs, potential interactions, and side-effects, via simple keyword based search.

In spite of the high amounts of knowledge about drugs and ADEs, it still remains a profound challenge for patients or even their physicians to discover relevant ADE knowledge. The "information barriers" those users face can be classified into three main types. First, users may be unaware of the existence of these sources. Second, many users, especially patients, usually are not familiar with drug and ADE terminology. Such users usually lack of the required technical skills for correctly expressing their information needs for accessing ADE knowledge, such as the one provided by DrugBank and SIDER. Third, the large amounts of data make it difficult for users to locate relevant and useful information for their needs.

BRIEF SUMMARY

According to a first aspect of the present invention there is provided a method for personalized medical content recommendation, comprising: having a patient medical profile; having a concept or relationship relating to the patient medical profile; obtaining medical content relevant to the concept or relationship; determining a score of the concept or relationship to the patient medical profile; enhancing the score with a context score based on the values of attributes of the concept or relationship in the patient medical profile; enhancing the score with an additional knowledge score based on knowledge of the concept or relationship additional to the medical content; recommending medical content with respect to a patient medical profile based on the enhanced scores; wherein said steps are implemented in either: computer hardware configured to perform said steps, or computer software embodied in a non-transitory, tangible, computer-readable storage medium.

The method may also include providing an explanation of a medical content recommendation based on a matching concept or relationship, including generating one or more explanation sentences based on the context score, and generating one or more explanation sentences based on the additional knowledge score.

According to a second aspect of the present invention there is provided a computer program product for personalized medical content recommendation, the computer program product comprising: a computer readable storage medium having computer readable program code embodied therewith, the computer readable program code comprising: computer readable program code configured to: have a patient medical profile; have a concept or relationship relating to the patient medical profile; obtain medical content relevant to the concept or relationship; determine a score of the concept or relationship to the patient medical profile; enhance the score with a context score based on the values of attributes of the concept or relationship in the patient medical profile; enhance the score with an additional knowledge score based on knowledge of the concept or relationship additional to the medical content; recommend medical content with respect to a patient medical profile based on the enhanced scores.

According to a third aspect of the present invention there is provided a system for personalized medical content recommendation, comprising: a processor; a patient medical profile receiver; a matched concept or relationship receiver; a medical content receiver for receiving medical content relevant to the concept or relationship; a scoring component for determining a score of the concept or relationship to the patient medical profile including: a context scoring component for providing a context score based on the values of attributes of the concept or relationship in the patient medical profile; and an additional knowledge scoring component for providing an additional knowledge score based on knowledge of the concept or relationship additional to the medical content.

According to a fourth aspect of the present invention there is provided a method of providing a service to a customer over a network, the service comprising: receiving a patient medical profile; receiving a concept or relationship relating to the patient medical profile; obtaining medical content relevant to the concept or relationship; determining a score of the concept or relationship to the patient medical profile; enhancing the score with a context score based on the values of attributes of the concept or relationship in the patient medical profile; enhancing the score with an additional knowledge score based on knowledge of the concept or relationship additional to the medical content; recommending medical content with respect to a patient medical profile based on the enhanced scores.

BRIEF DESCRIPTION OF THE SEVERAL VIEWS OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings in which:

Figure 1:
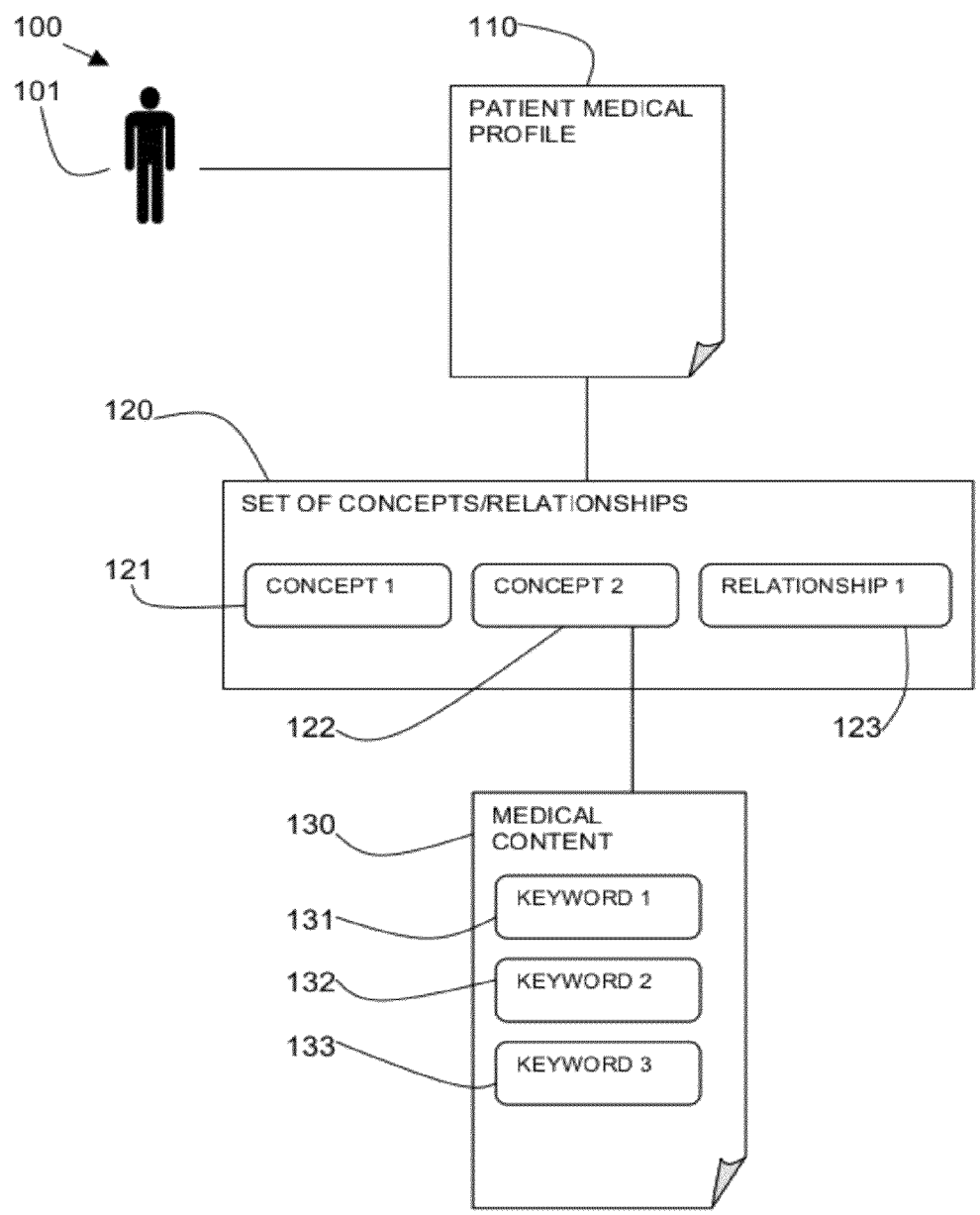
FIG. 1 is a schematic diagram illustrating concepts of a personalized medical content recommendation system in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The described approach helps to increase patient safety by exposing patients to relevant medical content (e.g., ADE related updates about new possible interactions among drugs, drugs and foods, drugs and medical conditions, new possible side effects of existing drugs, etc.) that is continuously gathered from various web sources, helping to better educate patients towards better preventive medicine decision making.

On top of existing medical content recommendation solutions, in the described system, relevant medical content recommendation is prioritized according to the medical context proximity to the personal health records of a patient and knowledge enhancement using existing internal and public knowledge bases that expand the recommender's extracted knowledge from the medical content.

A personalized ADE alerting service may reduce the time and efforts that both patients and physicians spend in finding relevant ADE information. Using the patient's health profile extracted from the patient's personal health records (PHR), which include personal information about the patient such as the list of medications that the patient is currently prescribed with, personalized ADE alerts can be delivered to the patient whenever relevant drug or ADE related content is being published in either of the sources. Patients may receive personalized alerts that inform them about potential risks and possibilities of ADEs given their up-to-date health profile. The ADE alerting service may further explain to the patients each recommendation, providing insights about what triggered each alert delivery. This in turn, helps patients to understand the lineage between their personal health profile and the content of the alert.

A personalized ADE alerting service can increase patient safety by turning patients attention toward relevant content regarding their health profile, further providing explanations about potential risks, which in turn may prevent future ADEs.

Medical content recommendation method and system are described that extend existing medical content recommendations.

Referring to FIG. 1, a schematic diagram 100 illustrates a patient p 101 for which a patient medical profile M 110 is provided.

A set 120 of concepts or relationships 121-123, C|M={c1, c2, ..., cm} may be determined which match to text fragments and concepts/relationships in the patient medical profile M 110. The concepts/relationships 121-123 may be scored for relevance to the patient medical profile M 110.

A medical content 130 such as a web page P may include keywords 131-133, T|M={t1, t2, ..., tn} which may be matched to the concepts/relationships 121-123. The medical content 130 may be recommended to a patient p 101 based on the match of the keywords 131-133 to the scored concepts/relationships 121-123.

Given a medical content 130, personalized medical content recommendation methods are extended which currently prioritize the recommendation of medical content 130 solely based on either textual or concept based (ontological) similarity to a given patient medical profile M 110.

Given a set of medical concepts and relationships 121-123 that are found to match a patient medical profile M 110 (e.g., using entity text extraction and content or ontology based recommendation methods) the described method and system further boost each concept or relationship relevance score using two new measures.

The first measure, named "MedicalContext", gets a concept/relationship 121-123 that was found to match the patient's medical profile 110 (e.g., using ontology-based recommendation or matching methods) and the original concept/relationship score and returns a new score that is a combination of the original relevance score and a new personalized boosting score that is based on medical context proximity between the matching concept/relationship to the patient's medical context with respect to that concept/relationship.

The second measure "KnowledgeEnhanced" gets a concept/relationship 121-123 that matches the patient medical profile 110 and the original concept/relationship score and returns a new score that is a combination of the original relevance score and a new boosting score derived from other medical knowledge about the concept/relationship and their prioritization level that is already known to exist in the system, but it may not be provided in the original medical content to be recommended.

Each medical content recommendation may be prioritized based on the combination of the two "MedicalContext" and "KnowledgeEnhanced" scores.

Similar to prioritization of recommended medical content, the two measures described above may be utilized for personalizing the explanations to patients and to provide additional patient safety details based on the medical context proximity and medical knowledge not disclosed in the original recommended medical content. The proposed explanation mechanism may get the set of matching concepts/relationships and may use two types of explanatory components to generate detailed and personalized medical content recommendation explanations. For a given matching concept/relationship, each explanatory component may return a set of one or more personalized explanation sentences in natural language that help the patient to understand better the lineage between his/her medical profile and the recommended medical content and gain more useful patient safety knowledge on top of that of the original medical content.

The first explanatory component "MedicalContextExplainer" may get as an input a matching concept/relationship and may generate one to many explanation sentences based on the "MedicalContext" score level of the concept or relationship.

The second explanatory component "KnowledgeEnhancedExplainer" may get as an input a matching concept/relationship and may generate one to many explanation sentences based on the "KnowledgeEnhanced" score level of the concept or relationship and the additional knowledge known to exist about the concept or relationship.

Figure 2:
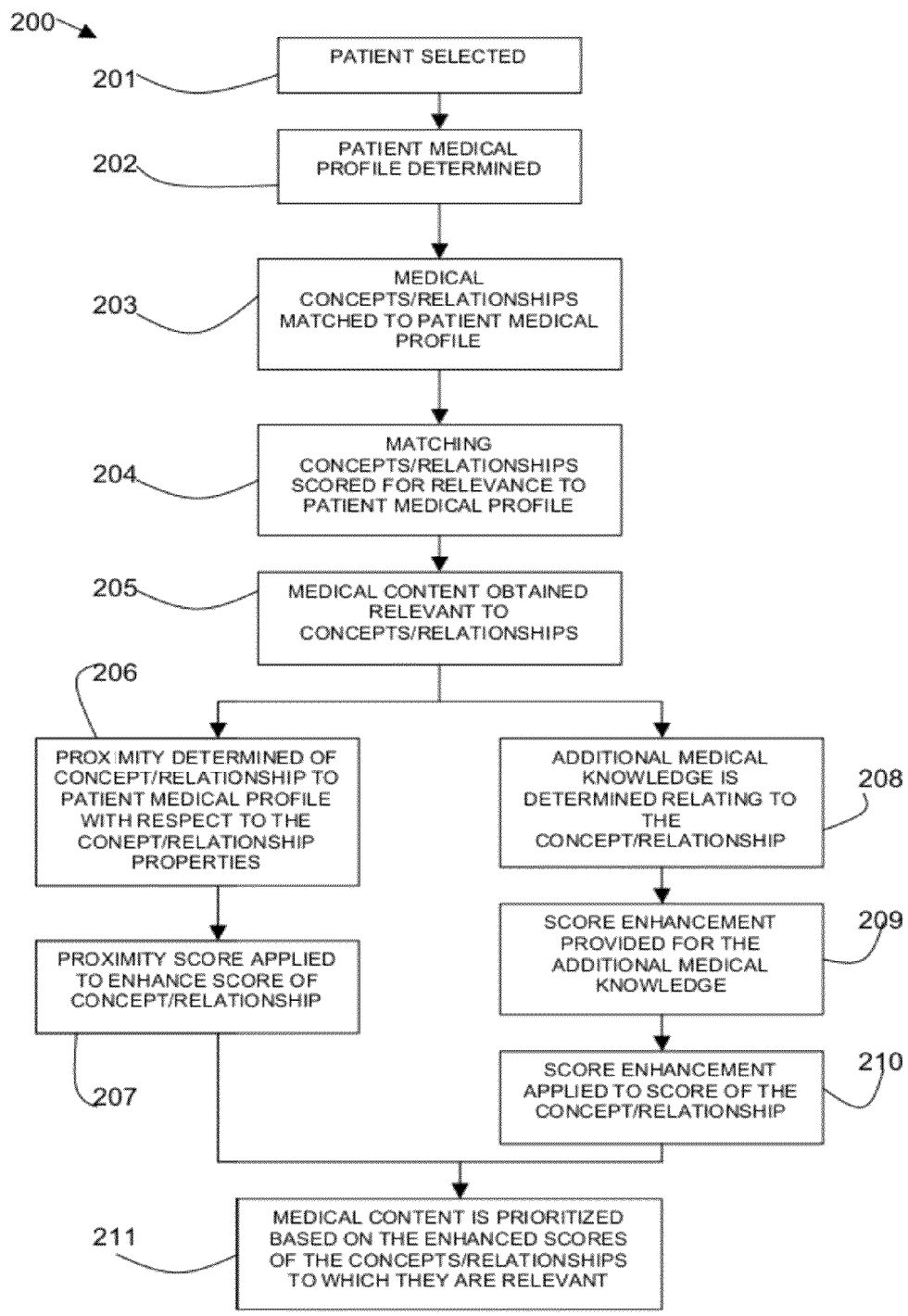
FIG. 2 is a flow diagram of a method of personalized medical content recommendation in accordance with the present invention.

Referring to FIG. 2, a flow diagram 200 shows an example method of personalized medical content recommendation.

A patient is selected 201 and a patient medical profile may be determined 202. A patient medical profile may be maintained for each patient and updated with information about the patient and his associations with various medical entities such as medicates, allergies, immunizations, various clinical conditions (e.g., pregnancy, diabetics, chronic diseases), and treatment plans, etc.

Medical concepts and relationships (e.g., a concept may be a medication, a condition, etc., and a relationship may be an interaction between medications, or an interaction between a condition and a medications, etc.) may be matched 203 to a patient medical profile (e.g., using ontology-based recommendation or matching methods). The matching concepts/relationships may be scored 204 for relevance to the patient medical profile.

Medical content may be obtained 205 which is relevant to the concepts/relationships of the patient. The medical content may be prioritized by using the score of the concept/relationship to which it is relevant.

A proximity measure may be determined 206 of a concept/relationship to the patient medical profile with respect to the concept/relationship properties. The proximity score may be applied 207 to enhance the score of the concept/relationship.

Additional medical knowledge may be determined 208 relating to the concept/relationship. If there is relevant additional medical knowledge a score enhancement may be provided 209 for the concept/relationship which may be applied 210 to the score of the content/relationship.

The medical content may be prioritized 211 for recommendation based on the enhanced scores of the content/relationship to which the medical content is relevant.

Figure 3:
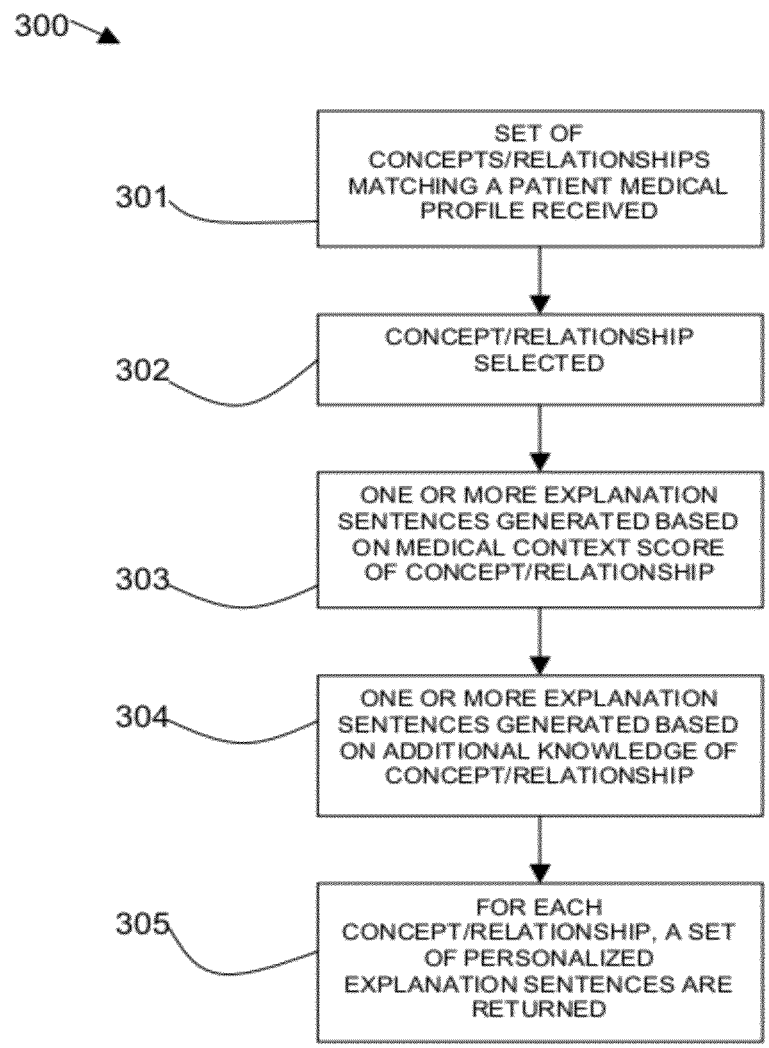
FIG. 3 is a flow diagram of a method of personalized medical content recommendation explanation in accordance with the present invention.

Referring to FIG. 3, a flow diagram 300 shows an example method of personalized medical content recommendation with enhanced explanation.

A set of concepts/relationships matching a patient medical profile may be received 301. A concept/relationship may be selected 302. One to many explanation sentences may be generated 303 based on the "MedicalContext" score level of the concept/relationship. One to many explanation sentences may be generated 304 based on the "KnowledgeEnhanced" score level of the concept/relationship. For each concept/relationship a set of personalized explanation sentences may be returned 305.

A system is described with reviews medical content, extracts concepts and text features from the content, and matches them against a given patient medical profile. An example embodiment of a system is described with reference to FIG. 4.

Figure 4:
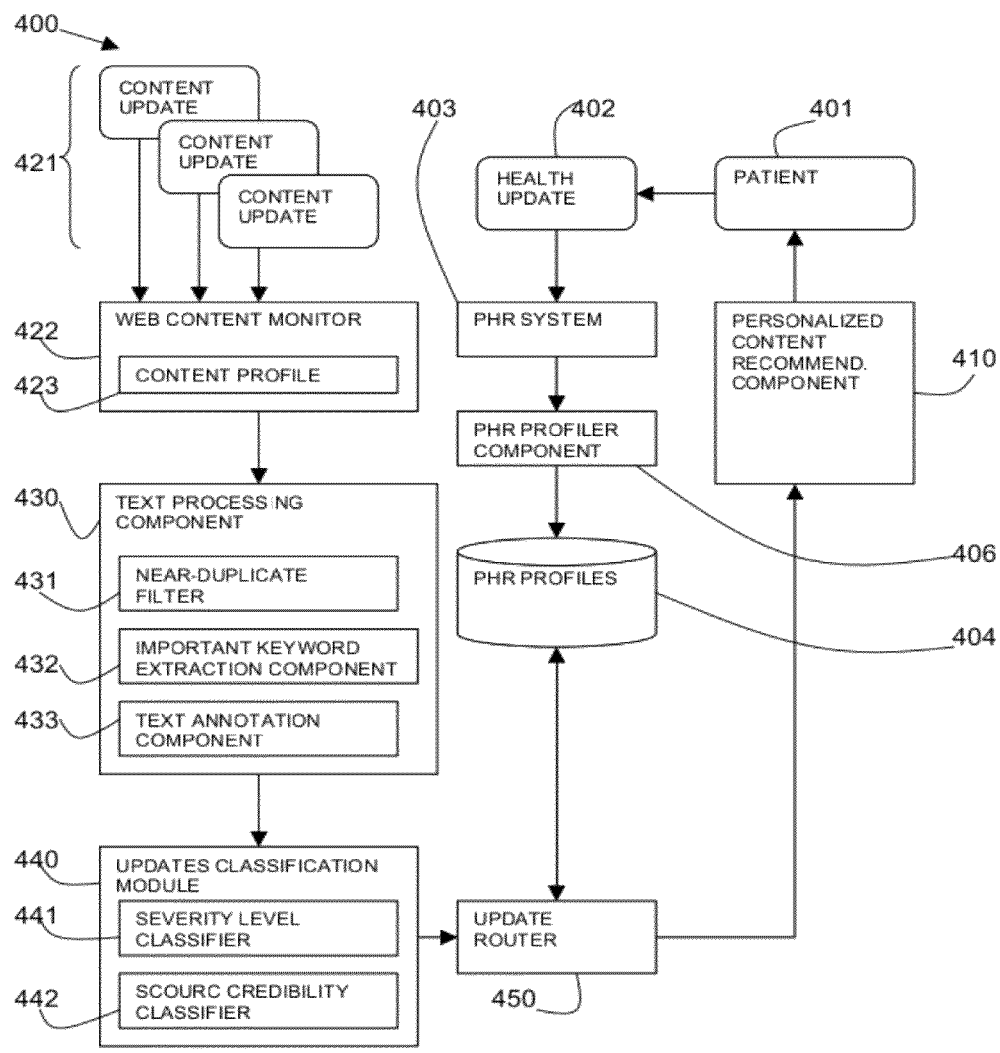
FIG. 4 is a block diagram of a personalized medical content recommendation system in accordance with the present invention.

FIG. 4 shows a block diagram of a system 400 including a personalized content recommender 410.

A patient 401 has health updates 402 which may be updated in a personal health records (PHR) system 403. A PHR profile 404 may be maintained for each patient in the system. Up-to-date PHR information updates about the clinical status of various patients in the system may be continuously delivered by the internal PHR system 403 to a PHR profiler component 406. In one embodiment, the PHR system may be HL7 RIM compatible, and updates may be delivered in HL7 Continuity of Care Document (CCD) format. Such updates may contain up-to-date information about patients and their associations with various medical entities, such as medications, allergies, immunizations, various clinical conditions (e.g., pregnancy, diabetics, chronic diseases), and treatment plans, etc.

In one embodiment, the PHR profiler component 406 may maintain an inverted index data structure that maps medical entities (and keywords) to their associated patient identities, sorted in ascending order to allow efficient aggregation during retrieval time.

For example, the following table shows an inverted index structure for two variations of Coumadin medication associated with two different patients.

| Medication/Coumadin | → | Patient 1 | → | Patient 2 |
|---|---|---|---|---|
| Medication/Coumadin/1 MG | → | Patient 1 | | |
| Medication/Coumadin/2 MG | → | Patient 2 | | |
| Medication/Paracetamol | → | | | |
| Medication/Warfarin | → | Patient 1 | → | Patient 2 |

Information content updates 421 may be continuously gathered from multiple health-related web sources (e.g., FDA MedWatch) using a web content monitor 422. The web content monitor 422 may be a server-side web feed aggregator, capable of monitoring a large number of web feeds (e.g., RSS) in parallel and provides efficient means for timely discovery of new updates, almost in real-time. The web content monitor 422 may alternatively be a web crawler that discovers medical related content by crawling the web.

The web content monitor 422 may also provide a unique and important service that maintains a content profile 423 for each monitored web source, which summarizes the content it publishes during a given time. Such source content profiles 423 may be utilized by an updates classification module 440 for determining the credibility of each source, which details are discussed next.

Updates 421 gathered by the web content monitor 422 may be delivered for text processing and classification. Such text analysis assists in the discovery of relevant patients for recommendation. It further helps to prioritize content recommendations and generate explanations for each recommendation.

A text processing component 430 may be responsible for processing each update content and enhancing it with additional text annotations which assist in matching updates with relevant patient PHR profiles 404. A near-duplicate filter 431 may filter out duplicate content. Some updates gathered from various sources may actually contain the same or almost the same content, i.e., near duplicates. This is usually true for updates gathered from different web sources that republish content that was already published by other referenced sources. Reducing near-duplicates is important in order to avoid "over-loading" patients with redundant information.

The text processing component 430 may also include an important keyword extraction component 432. Given the update text, its most representative keywords are extracted using feature selection methods. Representative keywords are usually those that are frequent in the update text and less frequent in the text of other updates. Focusing on such keywords reduces search efforts for locating relevant patients for recommendation.

The text processing component 430 may also include a text annotation component 433. Each update text is annotated using several information extraction techniques, such as named-entity recognition and part-of-speech tagging. For example, each update is annotated with all medical entities discovered in its text using UIMA clinical annotators, trained over several medical terminologies such SNOMED CT and ICD9. More complex semantic relationships between entities (e.g., drug interactions and drug side effects) are further discovered using ontologies, such as the ones provided by HCLS Linked Open Drug Data (LODD).

An updates classification component 440 may further classify each update according to the "severity level" of the details disclosed in its text, and the creditability of the update source. These two update properties help to determine the priority of each update for recommendation; i.e., the more severe is the disclosed update content, and the more credible is the update source, the higher priority assigned to this update for recommendation. A severity level classifier 441 may be provided to determine the severity level of each update by analyzing the update text, looking for the occurrence of specific dictionary terms that usually are used to describe severity, such as "death", "severe", "warning", etc. Each such dictionary term is assigned with some severity score. The update severity score may then be determined by the summing up the scores of occurring terms, relatively to their frequency, further normalized by the total term frequency in the update text. A source credibility classifier 442 may determine the credibility of each update source using several heuristics. First, given the content profile 423 (maintained by the web content monitor 422), its cosine distance may be measured from the current update text. The main idea here is that the smaller this distance is, the more focused is the update source in general on the main topic aspects disclosed by the current update, and therefore, this source is more credible with respect to that update. Source authority, based on link analysis and the amount of external meta-data associated with each source (e.g., number of bookmarks in Delicious), may also be used to determine source credibility.

An updates router 450 may be provided and, given an update, the PHR inverted index may help to efficiently map every important keyword or medical entity, extracted from the update text by the text processing component 430, to a list of matching patients. The inverted index further allows aggregation of the list of matching keywords and entities for each patient, which is used later on for prioritizing the update recommendation to each patient. Therefore, for each relevant patient, the result of this routing is a set of medical entities and keywords in the update text that satisfy the patient's PHR profile.

A personalized recommendation component 410 may be provided. Given a patient identity for recommendation, an update's content to be recommended to the patient, and the list of matching medical entities and keywords in the update content, the recommender component 410 may first prioritize the update according to the combination of its relevance to the patient's PHR profile, its severity, and its source credibility. Given the update to be recommended to the patient and its priority, the recommendation component 410 may also automatically generate an explanation for the patient, which accompanies the recommendation. This explanation's main goal is to provide enough details to the patient in order to help the patient to better understand the lineage between the patient's PHR profile and the recommended content.

A personalized priority for recommendation may be assigned to each update according to the medical entities and keywords that match the patient's PHR profile. In one embodiment, the priority score of each update u, given a matching patient PHR profile p may be calculated as follows:

$$\text{score}(u|p) = \text{rel}(u|p) \times \text{sev}(u) \times \text{cred}(u)$$

where rel(u|p) is the relevance score of update u given patient PHR profile p, sev(u) is the severity level of the details disclosed in update u, and cred(u) is the credibility of update u source.

The recommendation component may calculate for each patient a personalized relevance score rel(u|p) based on the similarity (e.g., cosine similarity) of the update content to the patient's PHR profile. The relevance score further boosts various matching medical entities according to their association strength with the patient. For example, a matching medication that the patient currently consumes, or an allergy that the patient currently suffers from, will be assigned with a relatively higher relevance score compared to all other matching entities. As another example, a medication that is consumed more often with higher dosage by the patient, will get a higher relevance score compared to a medication that the patient rarely takes. Therefore, content recommended to patients is always tailored to the most relevant personal health context of each patient.

Given a content for recommendation to some patient, the recommendation component may generate two types of explanations which help the patient to better understand the lineage between the recommended content to the patient's PHR profile. The first type, may be a summary of the update text, generated using traditional text summarization techniques, where every matching keyword or medical entity is further highlighted. Each matching medical entity may also be accompanied with a clickable icon that represents its type and provides a "quick-link" to that entity definition in the system's medical terminology. This in turn, allows the patient to overcome any difficulty in understanding the recommended content. The second type of explanations are sentences in natural language, one per each matching entity, which accompany the recommendation, and disclose to the patient the exact lineage between every matching entity in the recommended content and the patient's PHR profile.

A recommendation widget may be provided, for example, including alerts that are recommended to a patient in the system. For example, top recommended items may be FDA early communication alerts related to various medications that the patient is currently associated with. For example, a first recommended item, may alert the patient about possible Hepatic Effects related to the usage of Voltaren Gel (Voltaren is a trade mark of Novatis Consumer Health, Inc.). The next recommended item may alert the patient about a possible interaction between the Ibuprofen and Aspirin drugs, that are two medications that the patient currently uses.

The personalized content recommendation component 410 described with reference to FIG. 4 is extended to include an enhanced scoring, prioritization of medical content, and an enhanced explanation generation component.

Figure 5:
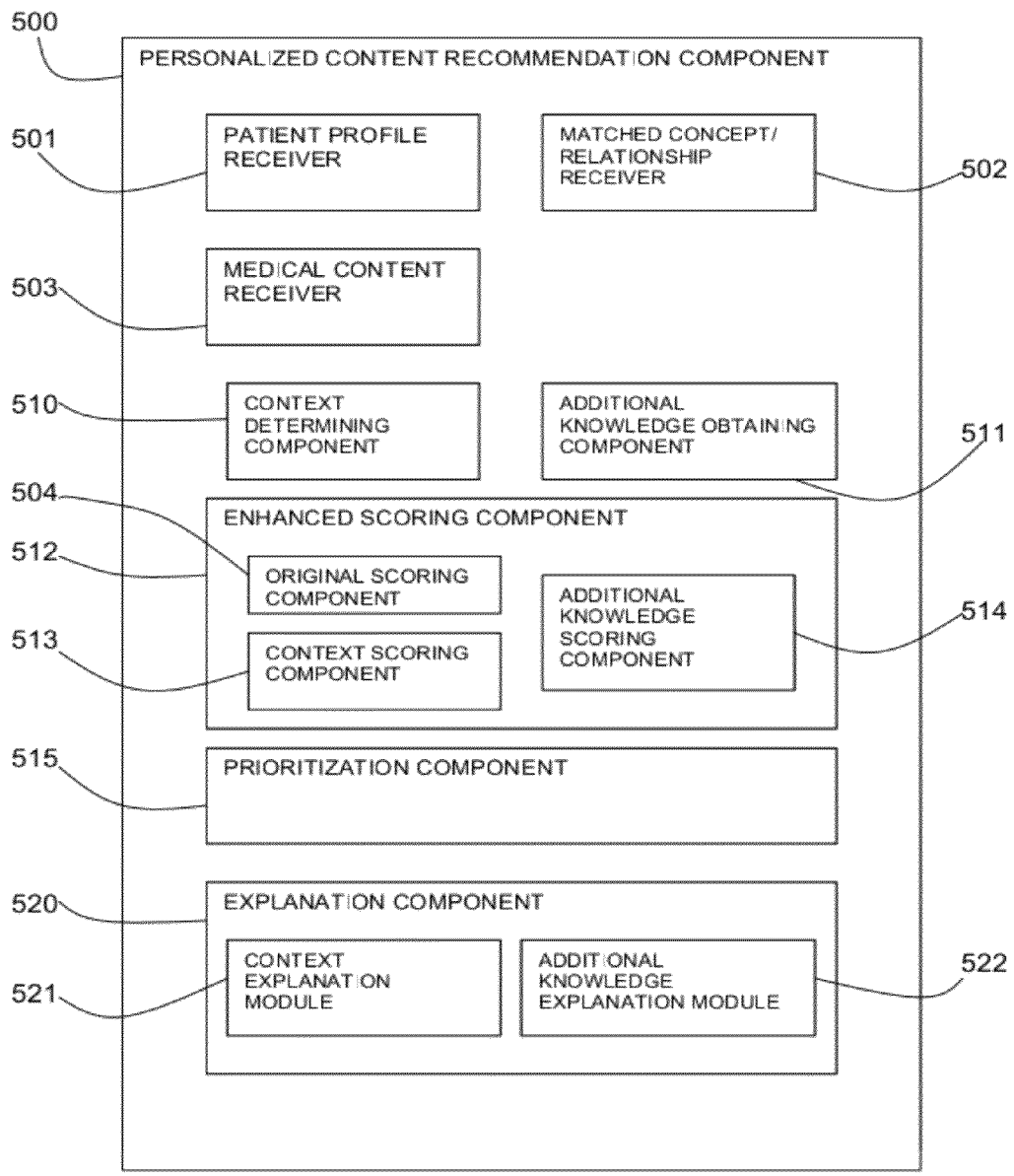
FIG. 5 is a block diagram showing further details of the personalized medical content recommendation system of FIG. 4.

Referring to FIG. 5, an embodiment of an enhanced personalized content recommendation component 500 is shown. The recommendation component 500 may include a patient profile receiver 501 for receiving a patient medical profile for a selected patient. A matched concepts/relationships receiver 502 may be provided for receiving or generating concepts/relationships matching a patient medical profile.

A medical content receiver 503 may be provided for receiving relevant medical content relating to the matched concepts/relationships of a patient medical profile. A context determining component 510 may be provided for determining a proximity of a concept/relationship to a patient medical profile with respect to the concept/relationship property values in the patient medical profile.

An additional knowledge obtaining component 511 may be provided for obtaining additional external resources relating to a concept/relationship.

A scoring component 512 may be provided for scoring the received medical content. The scoring component 512 may include an original scoring component 504 for providing a basic score for medical content. For example, the received medical content may be scored as described above with respect to the relevance, severity, and credibility of the medical content.

In order to provide enhanced scoring of the medical content for recommendation for a patient, the scoring component 512 may also include a context scoring component 513 and an additional knowledge scoring component 514.

A prioritization component 515 may be provided for prioritizing medical content for a selected patient according to the results of the scoring component 512.

In addition, an explanation component 520 may be provided including a context explanation module 521 and an additional knowledge explanation module 522.

Figure 6:
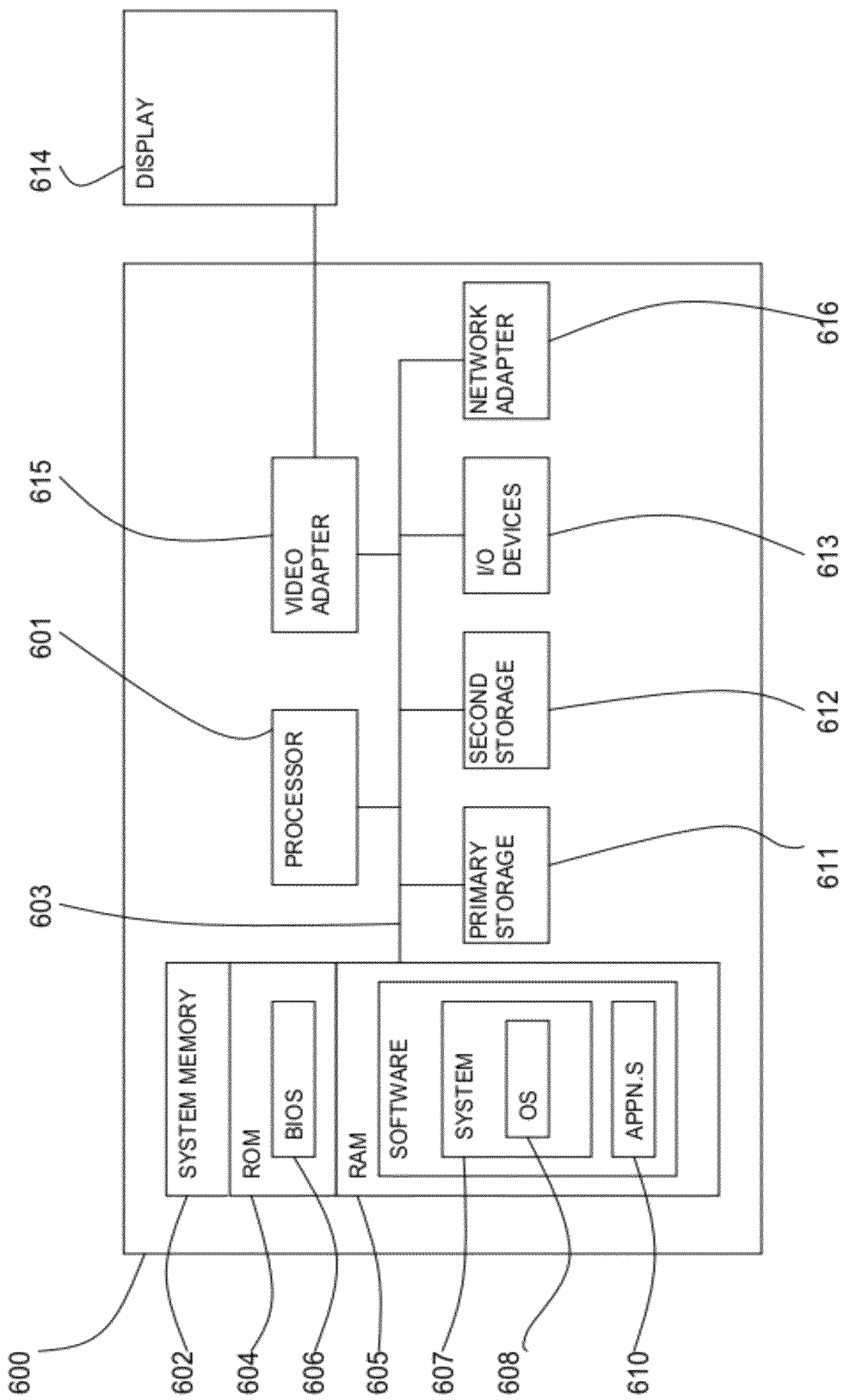
FIG. 6 is a block diagram of a computer system in which the present invention may be implemented.

Referring to FIG. 6, an exemplary system for implementing aspects of the invention includes a data processing system 600 suitable for storing and/or executing program code including at least one processor 601 coupled directly or indirectly to memory elements through a bus system 603. The memory elements can include local memory employed during actual execution of the program code, bulk storage, and cache memories which provide temporary storage of at least some program code in order to reduce the number of times code must be retrieved from bulk storage during execution.

The memory elements may include system memory 602 in the form of read only memory (ROM) 604 and random access memory (RAM) 605. A basic input/output system (BIOS) 606 may be stored in ROM 604. System software 607 may be stored in RAM 605 including operating system software 608. Software applications 610 may also be stored in RAM 605.

The system 600 may also include a primary storage means 611 such as a magnetic hard disk drive and secondary storage means 612 such as a magnetic disc drive and an optical disc drive. The drives and their associated computer-readable media provide non-volatile storage of computer-executable instructions, data structures, program modules and other data for the system 600. Software applications may be stored on the primary and secondary storage means 611, 612 as well as the system memory 602.

The computing system 600 may operate in a networked environment using logical connections to one or more remote computers via a network adapter 616.

Input/output devices 613 can be coupled to the system either directly or through intervening I/O controllers. A user may enter commands and information into the system 600 through input devices such as a keyboard, pointing device, or other input devices (for example, microphone, joy stick, game pad, satellite dish, scanner, or the like). Output devices may include speakers, printers, etc. A display device 614 is also connected to system bus 603 via an interface, such as video adapter 615.

For the following description, let M be the medical profile of some patient p. Given a web page P, let $T|M=\{t1, t2, \ldots, tn\}$ be a set of matching keywords extracted from the text of P and let $C|M=\{c1, c2, \ldots, cm\}$ be a set of matching (ontological) concepts/relationships (e.g., based on SNOMED CT, ICD9, etc) to text fragments (e.g., concept labels/descriptions) and concepts/relationships in the patient medical profile M. Without loss of generality, both keywords and concepts/relationships are treated as ontological constructs, and therefore, concepts and relationships are focused on.

Boosting the Personalization of Medical Content Recommendation:

Given a medical textual content personalized medical content recommendation methods may be extended which prioritize the recommendation of medical content based on either textual or concept based (ontological) similarity to a given patient's profile.

Given a set of medical concepts and relationships that were found to match the patient's profile C|M (e.g., using state of the art content or ontology based recommendation) each concept or relationship relevance score is boosted using two new measures.

For a given matching concept, two recommendation boosting measures may be defined, "MedicalContext" and "KnowledgeEnhanced".

The "MedicalContext" measure, may get a concept or a relationship in C|M that was found to match the patient medical profile and the original concept or relationship score (denoted org_score(c)) and returns a new score that is a combination of the original relevance score and a new personalized boosting score that is based on medical context proximity between the matching concept/relationship to the patient's medical context with respect to that concept/relationship.

The details of this measure are now described, separating into to two distinct cases according to the ontological construct type, either a concept or a relationship.

Case 1 (concepts): Formally, let c be a matching concept in C|M. It is assumed that each such concept may have several attributes whose values are specific to the patient's personalized medical profile M context (denoted context(M)). For example, for a matching medication, there may be attributes of generic name, brand name, medication dosage (e.g., 20 mg), medication consumption, active time interval, medication consumption frequency (e.g., twice a day), and medication consumption route. For such concept c, the MedicalContext measure returns a score that is based on that concept original score combined with a new score calculated as a function of the concept's attribute values as given by the patient's personalized medical context.

As a concrete example, given a matching medication c with some original score org_score(c), the relevance of this concept to the patient's medical profile is boosted based on that medication concept's medical context attributes. For example, medications may need to be boosted that are consumed: more often, with higher dosage amount, or are actively consumed as given by time proximity of current time to the interval of the medication consumption.

For this specific example, a MedicalContext score may be defined as follows:

$$\text{MedicalContext}(\text{Medication}|\text{context}(M)) = \text{org\_score}(\text{Medication}) * \text{Medication.dosage} * \exp\hat{}\{-(\text{now}-\text{Medication.end\_time})/\text{Medication.frequency}\}$$

Case 2 (relationship): Formally, let R(c1,c2) be a relationship described to exist in medical content P between two concepts c1 and c2. For example, a possible relationship may be InteractsWith(Medication1,Medication2) which captures the possible ADE interaction between two medications found to be matched to the patient's medical profile M.

For such relationship R(c1,c2), MedicalContext returns a score that is based on the original score of concepts c1 and c2 combined with a new score for relationship R calculated based on the personalized patient's medical context. For example, for the R(c1,c2)=InteractsWith(Medication1,Medication2) relationship the following score may be used:

$$\text{MedicalContext}(\text{InteractsWith}(\text{Medication1},\text{Medication2})|\text{context}(M)) = \text{org\_score}(\text{InteractsWith}(\text{Medication1},\text{Medication2})) * (\text{Intersect}(\text{Medication1.time\_interval},\text{Medication2.time\_interval})?1:0)$$

The above example score function can be used to make sure that relevance scores for matching interaction relationships between patient's medications will effect the prioritization of the medical content recommendation if there is a real chance of intersection between the two medications active consumption intervals, as can be derived from the patient's medical context, confirming that indeed there is a chance that the patient may consume the two medications together. Therefore, the recommendation system should consider this interaction as relevant to this patient.

"KnowledgeEnhanced" measure gets a concept or a relationship in C|M that matches the patient's medical profile and the original concept or relationship score and returns a new score that is a combination of the original relevance score and a score derived from other medical knowledge about the concept or relationship and their prioritization level that are already known to exist in the system, but is not provided in the original medical content to be recommended.

The details of this measure are now described separated into two distinct cases according to the ontological construct type, either a concept or a relationship.

Case 1 (concepts): For a given concept, this measure tries to expand the knowledge known about it and derives additional concepts based on rules, synonyms, acronyms, ontological similarity, thesaurus, dictionaries (e.g., WordNet), etc. For example, given that an original concept is c="Teenage Pregnancy" this measure detects that it is related to the following complex combination of ontological concepts (12<Patient.age<18) AND (Patient.gender=Female) AND (Patient.isCurrentlyPregnant=true).

Given the set of expanded concepts, this measure then use the KnowledgeEnhanced measure to calculate a score for concept c. For example: KnowledgeEnhanced("Teenage Pregnancy"|context(M))=org_score("Teenage Pregnancy")* ((12<Patient.age<18? 1:0)*(Patient.gender=Female? 1:0)* (Patient.isCurrentlyPregnant=true? 1:0)

The above example score function will assign the original score to that concept if it is relevant according to the patient's medical context.

Note that before the knowledge enhancement phase, it is not possible to know the relevant medical contexts that should be considered, and therefore, recommending medical content based on this concept textual match alone may generate a false alarm.

Case 2 (relationships): For a given relationship R(c1,c2), this measure tries to expand the knowledge known about it and derives facts about the relationship additionally to the facts known to exist about it in the original medical content from which this relationship was extracted.

For example, for the InteractsWith(Medication1,Medication2) relationship, it is assumed that the medical content also included details of a possible side-effect "SideEffect" that may be the result of the described drug interaction. Given this interaction relationship, this measure will utilize any existing knowledge (e.g., the SIDER Linked Open Drug Data (LODD) knowledgebase) to discover whether that specific interaction has more side effects known for that specific drug interaction which is not disclosed in the original medical content to be recommended. Therefore, in case additional side effects exist for that drug interaction, this measure will boost more the relevance score of that interaction to the patient's medical profile.

For example:

$$\text{KnowledgeEnhanced}(\text{InteractsWith}(\text{Medication1},\text{Medication2}),\text{SideEffect}|\text{context}(M)) = \text{org\_score}(\text{InteractsWith}(\text{Medication1},\text{Medication2})) * (2\hat{}\#\{\text{known side effects for InteractsWith}(\text{Medication1},\text{Medication2})\text{excluding SideEffect}\})$$

In the above example score function, the original score of the drug interaction described in the medical content will be power-lawed boosted proportionally to the number of additional side-effects known to exist given external knowledge on that interaction. If none such exist the boosted score converge to the original score ($2\hat{}0=1$).

An extension to this specific measure would be to utilize the known risk levels of each side-effect, i.e., further multiply each side effect by the risk level that it has (e.g., Death=1000).

Finally, each medical content recommendation is prioritized based on the combination of the two new MedicalContext and KnowledgeEnhanced scores.

Explanation of Medical Content Recommendation Based on Medical Context Proximity and Knowledge Enhancement Similar to prioritization of recommended medical content the two measures described above may be utilized for personalizing the explanations to patients and to provide additional patient safety details based on medical knowledge not disclosed in the original recommended medical content. The proposed explanation mechanism gets the set of matching concepts/relationships and uses two types of explanatory components to generate detailed and personalized medical content recommendation explanations.

For a given matching concept/relationship, each explanatory component returns a set of one or more personalized explanation sentences in natural language that help the patient to better understand the lineage between his/her medical profile and the recommended medical content and gain more useful patient safety knowledge on top of that of the original medical content.

Explanation Based on Medical Context (Proximity Score)

The first explanatory component "MedicalContextExplainer" gets as an input a matching concept or relationship and generates one to many explanation sentences based on the MedicalContext score level of the concept or relationship.

As a concrete example, an explanation for some medication that matches the patient's medical profile may be generated based on the medical context attribute values of that medication. For example a patient that actively consumes a matching medication more often will get an explanation message as follows:

"This recommended medical content mentions Voltaren 20 mg Gel which is a medication that you currently use 2 times a day".

This is in comparison to a patient who according to his/her medical context does not actively consume the medication but used to in the past:

"This recommended medical content mentions Voltaren 20 mg Gel which is a medication that you used lately (about 2 weeks ago)".

Explanation Based on Knowledge Enhancement (Score)

The second explanatory component "KnowledgeEnhancedExplainer" gets as an input a matching concept or relationship and generates one to many explanation sentences based on the KnowledgeEnhanced score level of the concept or relationship and the additional knowledge known to exist about the concept or relationship.

As a concrete example, for a given matching interaction, an explanation that contains additional side effect knowledge about the interaction may be generated:

"This recommended medical content mentions an interaction between two drugs Ibuprofen and Aspirin which you actively consume and which may lead to the following side effects: [original side effect mentioned in the medical content], [additional known side effects given the system's external knowledge]. Please consult with your physician as soon as possible".

Further note that in this specific example, medical context was used to determine that the patient actively consumes the two medications.

In case the patient does not actively consume the two medications but used to consume either of them in the past, the following explanation message may be generated for that specific drug interaction:

"This recommended medical content mentions an interaction between two drugs Ibuprofen and Aspirin which you used to consume in the past. Please note that consuming the two drugs together may lead to the following side effects: [original side effect mentioned in the medical content], [additional known side effects given the system's external knowledge]".

On top of existing solutions, a solution for personalized content recommendation is provided based on patient personal health records (PHR), which is better tailored for the patient safety domain. A content recommendation scheme provides personalization using precise medical context and enhanced knowledge. An explanation mechanism for the patient safety domain is based on medical context and knowledge enhancement. Based on the level of relevance to the patient medical context, detailed explanations may be generated to explain the lineage of each relevant medical content to the patient.

Existing solutions ignore medical context, and therefore may overload patients with false alarm medical content recommendations. Precise medical content recommendation and reduction of false alarms is especially important in the domain of ADE content recommendation, where mistakes in medical recommendation may cause patients to ignore physicians medical treatment recommendations or even stop the consumption of their drugs which may lead to further undesired outcomes.

The proposed solution is capable of extending any existing medical content recommendation solution with medical context and additional knowledge which in turn helps to prioritize the content recommendation, reduce false alarms, better personalize the recommendations, and educate patients towards better medicine preventative decision making.

In addition, existing systems prioritize medical content recommendations based solely on the knowledge that is embedded in the content itself and do not try to expand the knowledge extraction from the text with existing medical knowledge (e.g., to discover that additional side effects are known to exist for some reported drug interaction in the medical content to be recommended).

Furthermore, using existing solutions, it is usually very hard for ordinary patients with no prior background to understand the exact (or approximate) lineage between their medical context and the recommended medical content.

Current existing medical content recommendation systems provide only simple IR-based text highlighting, similar to highlight of search results, making it hard for patients to clearly understand the lineage of the recommended medical content to their medical context and how to utilize the recommended medical content for increasing their safety and in what situations.

A personalized medical content recommendation system may be provided as a service to a customer over a network.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for personalized medical content recommendation, comprising:
    accessing, from a data storage medium, a patient's medical profile, a concept or relationship relating to the patient's medical profile, and medical content relevant to the concept or relationship,
    wherein the concept or relationship is determined worthy of attention and possible reporting to the patient due to recognizing a level of risk to the patient based on an analysis of the patient's medical profile, the concept or relationship and the relevant medical content;
    determining, via one or more processors, a score for the concept or relationship to the patient's medical profile;
    enhancing, via one or more processors, the score using a medical context score wherein the enhanced medical context score is determined based on a proximity measure between the concept or relationship and potential intersections that can be formed by the concept or relationship;
    enhancing, via one or more processors, the score with an additional knowledge score wherein the enhanced additional knowledge score is determined based on one or more risk levels associated with the concept or relationship and additional medical knowledge that is obtained by searching external sources for medical content relevant to the concept or relationship; and
    recommending medical content with respect to a patient medical profile based on the enhanced scores,
    wherein the medical content is sorted in a first order according to level of risk to the patient.

2. The method as claimed in claim 1, wherein a concept is one of the group of: a medication, a medical condition, an allergy, an immunization, a treatment plan, a vital sign, a medical test result, a food, a patient symptom.

3. The method as claimed in claim 1, wherein a relationship is an interaction between concepts.

4. The method as claimed in claim 1, including:
    providing an explanation of a medical content recommendation based on a matching concept or relationship.

5. The method as claimed in claim 4, including:
    generating one or more explanation sentences based on the medical context score.

6. The method as claimed in claim 4, including:
    generating one or more explanation sentences based on the additional knowledge score.

7. A computer program product comprising a non-transitory data storage medium with logic code embedded therein, wherein execution of the logic code by a computer causes the computer to:
- access, from a data storage medium, a patient's medical profile, a concept or relationship relating to the patient's medical profile, and medical content relevant to the concept or relationship,
- wherein the concept or relationship is determined worthy of attention and possible reporting to the patient due to recognizing a level of risk to the patient based on an analysis of the patient's medical profile, the concept or relationship and the relevant medical content;
- determine, via one or more processors, a score for the concept or relationship to the patient's medical profile;
- enhance, via one or more processors, the score using a medical context score wherein the enhanced medical context score is determined based on a proximity measure for the concept or relationship and potential intersections formed by the concept or relationship;
- enhance, via one or more processors, the score with an additional knowledge score wherein the enhanced additional knowledge score is determined based on one or more risk levels associated with the concept or relationship and additional medical knowledge that is obtained by searching external sources for medical content relevant to the concept or relationship; and
- recommend medical content with respect to a patient medical profile based on the enhanced scores,
- wherein the medical content is sorted in a first order according to level of risk to the patient.

8. A system for personalized medical content recommendation, comprising:
- a processor adapted to access, from a data storage medium, a patient's medical profile, a concept or relationship relating to the patient's medical profile, and medical content relevant to the concept or relationship,
- wherein the concept or relationship is determined worthy of attention and possible reporting to the patient due to recognizing a level of risk to the patient based on an analysis of the patient's medical profile, the concept or relationship and the relevant medical content;
- a processor adapted to determine a score for the concept or relationship to the patient's medical profile;
- a processor adapted to enhance the score using a medical context score wherein the enhanced medical context score is determined based on a proximity measure between the concept or relationship and potential intersections formed by the concept or relationship;
- a processor adapted to enhance the score with an additional knowledge score wherein the enhanced additional knowledge score is determined based on one or more risk levels associated with the concept or relationship and additional medical knowledge that is obtained by searching external sources for medical content relevant to the concept or relationship; and
- a processor adapted to recommend medical content with respect to a patient medical profile based on the enhanced medical context and additional knowledge scores,
- wherein the medical content is sorted in a first order according to level of risk to the patient.

9. The system as claimed in claim 8, including:
- a context determining component for determining values of attributes of the concept or relationship in the patient medical profile.

10. The system as claimed in claim 8, wherein a concept is one of the group of: a medication, a medical condition, an allergy, an immunization, a treatment plan, a vital sign, a medical test result, a food, a patient symptom.

11. The system as claimed in claim 8, wherein a relationship is an interaction between concepts.

12. The system as claimed in claim 8, including:
- an explanation component for providing an explanation of a medical content recommendation based on a matching concept or relationship.

13. The system as claimed in claim 12, wherein the explanation component includes generating one or more explanation sentences based on the context score.

14. The system as claimed in claim 12, wherein the explanation component includes generating one or more explanation sentences based on the additional knowledge score.

15. A method of providing a service to a customer over a network, the service comprising:
- retrieving, from a non-transitory data storage medium, a patient's medical profile, a concept or relationship relating to the patient's medical profile, and medical content relevant to the concept or relationship, using one or more processors,
- wherein the concept or relationship is determined worthy of attention and possible reporting to the patient due to recognizing a level of risk to the patient based on an analysis of the patient's medical profile, the concept or relationship and the relevant medical content;
- determining, via one or more processors, a score for the concept or relationship to the patient's medical profile;
- enhancing, via one or more processors, the score using a medical context score wherein the enhanced medical context score is determined based on a proximity measure between the concept or relationship and potential intersections formed by the concept or relationship;
- enhancing, via one or more processors, the score with an additional knowledge score wherein the enhanced additional knowledge score is determined based on one or more risk levels associated with the concept or relationship and additional medical knowledge that is obtained by searching external sources for medical content relevant to the concept or relationship;
- recommending medical content with respect to a patient medical profile based on the enhanced medical context and additional knowledge scores,
- wherein the medical content is sorted in a first order according to level of risk to the patient.

* * * * *